United States Patent
Adachi

(10) Patent No.: US 8,598,485 B2
(45) Date of Patent: Dec. 3, 2013

(54) STAGE FOR WORKING, FOCUSED BEAM WORKING APPARATUS AND FOCUSED BEAM WORKING METHOD

(75) Inventor: Tatsuya Adachi, Chiba (JP)

(73) Assignee: SII Nano Technology Inc., Chiba (JP)

( * ) Notice: Subject to any disclaimer, the term of this patent is extended or adjusted under 35 U.S.C. 154(b) by 1464 days.

(21) Appl. No.: 11/849,705

(22) Filed: Sep. 4, 2007

(65) Prior Publication Data

US 2008/0029492 A1 Feb. 7, 2008

Related U.S. Application Data

(63) Continuation of application No. PCT/JP2006/302989, filed on Feb. 21, 2006.

(30) Foreign Application Priority Data

Mar. 4, 2005 (JP) .................................. 2005-060110

(51) Int. Cl.
| | |
|---|---|
| *B23K 15/00* | (2006.01) |
| *H01J 37/20* | (2006.01) |
| *H01J 37/315* | (2006.01) |

(52) U.S. Cl.
USPC ............ 219/121.13; 219/121.14; 219/121.18; 219/121.2; 250/492.21

(58) Field of Classification Search
USPC ............. 219/121.67–121.69, 121.72, 121.82, 219/121.31, 121.19, 121.2; 250/440.11, 250/442.11, 492.3, 311, 492.21; 269/55, 269/58, 71, 46, 9; 414/147, 331.01–331.03, 414/332, 444–447; 977/882
See application file for complete search history.

(56) References Cited

U.S. PATENT DOCUMENTS

| | | | | |
|---|---|---|---|---|
| 2,355,684 | A | * | 8/1944 | Skipper ........................... 409/66 |
| 2,948,087 | A | * | 8/1960 | Caton ........................... 451/271 |
| 2,969,553 | A | * | 1/1961 | Hatherell et al. ............... 470/46 |
| 3,342,994 | A | * | 9/1967 | Langerhorst et al. .... 250/442.11 |
| 3,446,960 | A | * | 5/1969 | Eubanks et al. .............. 250/397 |
| 4,058,731 | A | * | 11/1977 | Muller et al. ............ 250/442.11 |

(Continued)

FOREIGN PATENT DOCUMENTS

| | | |
|---|---|---|
| JP | 9-223477 A | 8/1997 |
| JP | 2000-162102 A | 6/2000 |

(Continued)

OTHER PUBLICATIONS

Office Action issued Jun. 24, 2008 in Japanese patent application No. 2005-060110 (with translation).

*Primary Examiner* — Samuel M Heinrich
(74) *Attorney, Agent, or Firm* — Brinks Gilson & Lione

(57) ABSTRACT

The present invention efficiently processes work pieces by transferring them without bringing them outside. The present invention comprises: a stage 4 for working, which is used when working a work piece D, L by irradiating a focused beam B while observing the work piece D, L in an observation region W of a previously determined range, and possessing a table 10 having plural mount bases 2, 3 on whose upper faces 2a, 3a there can be respectively mounted the work piece D, L; and a rotation slant means 11 rotating respectively the mount base 2, 3 about a Z-axis perpendicular to the upper faces 2a, 3a and slanting the upper faces 2a, 3a to an arbitrary angle, wherein the table 10 is made possible to move so as to dispose respectively the plural mount bases 2, 3 to an inside of the observation region W.

5 Claims, 3 Drawing Sheets

(56) References Cited

U.S. PATENT DOCUMENTS

| | | | |
|---|---|---|---|
| 4,589,174 A * | 5/1986 | Allen | 29/33 R |
| 4,837,444 A * | 6/1989 | Ohi | 250/442.11 |
| 5,028,780 A * | 7/1991 | Kaito et al. | 250/307 |
| 5,329,732 A * | 7/1994 | Karlsrud et al. | 451/289 |
| 5,628,111 A * | 5/1997 | Iwasaki et al. | 29/841 |
| 6,538,254 B1 * | 3/2003 | Tomimatsu et al. | 250/442.11 |
| 6,717,156 B2 * | 4/2004 | Sugaya et al. | 250/440.11 |
| 6,786,686 B1 * | 9/2004 | Koike | 409/235 |
| 6,870,161 B2 * | 3/2005 | Adachi et al. | 250/311 |
| 6,927,838 B2 * | 8/2005 | Ono et al. | 355/72 |
| 6,963,068 B2 * | 11/2005 | Asselbergs et al. | 250/311 |
| 7,491,022 B2 * | 2/2009 | Kato et al. | 409/221 |
| 7,566,884 B2 * | 7/2009 | Deguchi et al. | 250/442.11 |
| 2003/0183776 A1 | 10/2003 | Tomimatsu et al. | |

FOREIGN PATENT DOCUMENTS

| | | |
|---|---|---|
| JP | 2001-66231 A | 3/2001 |
| JP | 2001-176442 A | 6/2001 |
| JP | 2004-245660 A | 9/2004 |
| JP | 2004-301853 A | 10/2004 |
| JP | 2004-309499 A | 11/2004 |
| WO | WO 99/05506 A1 | 2/1999 |

* cited by examiner

STAGE FOR WORKING, FOCUSED BEAM WORKING APPARATUS AND FOCUSED BEAM WORKING METHOD

This application is a continuation of PCT/JP2006/302989 filed Feb. 21, 2006, which claims priority to Japanese Application No. JP2005-060110 filed Mar. 4, 2005. The entire contents of these applications are incorporated herein by reference.

BACKGROUND OF THE INVENTION

1. Technical Field

The present invention relates to a stage for working, a focused beam working apparatus having the stage for working, and a focused beam working method, which are used when working a work piece by irradiating a focused beam while observing the work piece in an observation region of a previously determined range.

2. Background Information

In recent years, there has been an increased demand in technical developments in a nano-(nm)-region in semiconductor technology. For example, a technique exists in which, for a trial manufacture or an analysis of semiconductor, bio-chip, micro-machine (MEMS) or the like, a sample of a wafer or the like is sectioned to make a very fine section sample (work piece), and the section sample is observed by a transmission electron microscope (TEM) having a high observation resolving power.

Although this section sample for being observed by the TEM, i.e., sample for TEM, is produced by various methods, recently a method of producing it by an FIB device utilizing a focused ion beam (FIB) has become common. In addition, the section sample produced by the FIB device is observed with a high resolving power after being relocated onto a stage of a TEM device.

However, as mentioned above, in order to observe the section sample, it is necessary to relocate the section sample produced by the FIB device to the stage of the TEM device. Therefore, the operation was troublesome and required time between reaching the TEM observation and production of the section sample. In particular, after being observed, if additional re-work of the section sample was attempted, relocation was necessary again, resulting in further trouble and requiring further time. Further, extra care was required such that a loss of the section sample, or the like, did not occur when relocating the section sample.

In order to solve the issues like these, there is known a sample production apparatus in which the operation from the production of the section sample though observation is simple, and the production of the section sample can be performed in one apparatus and the produced section sample can be easily transferred (relocated) to an analysis device (e.g., refer to JP-A-2004-301853 and JP-A-2004-309499).

This sample production apparatus possesses a sample stage fine-movement means attached to a sample chamber whose inside is adjustable to a vacuum state, a first stage that may be inserted into the sample chamber through the sample stage fine-movement means and can mount a sample piece, a second stage capable of mounting an extraction sample (section sample) produced from one part of the sample piece, a transfer means relocating the extraction sample to the second stage from the first stage in the sample chamber, and various constituent articles producing the section sample from the sample piece or forming a deposition film in the sample chamber, and the like.

Further, the second stage is made such that, under a state mounting the extraction sample, it can be inserted into a stage introduction port of other analysis device, e.g., the transmission electron microscope (TEM), a scanning electron microscope (SEM), a secondary ion mass spectrometry (SIMS) device, or the like.

In this sample production apparatus, first, the first stage is inserted into the sample chamber through the sample stage fine-movement means, and the extraction sample is produced from the mounted sample piece. And, after gripping the produced extraction sample by the transfer means, the first stage is pulled out of an inside of the sample chamber and the second stage is inserted. At this point a vacuum state in the sample chamber is maintained. After the insertion of the second stage, the transfer means mounts the gripped extraction sample mount onto the second stage. Incidentally, the gripping and the mounting, to the second stage, of the extraction sample are performed by utilizing the deposition film. After the extraction sample is mounted to the second stage, the extraction sample can be easily relocated by pulling out the second stage and inserting it to a stage insertion port of another analysis device, e.g., the TEM device, thus reducing labor and time of the operation. Further, since it is unnecessary to directly contact the sample piece with a hand after the sample piece is mounted to the first stage, it is possible to void loss of the sample piece.

Non-Patent Document 1: "Saishin Doukou of MEMS.MEMS Technique" Tore Research Center, 2004, Published in 2005 May However, in the above conventional method, the following problems are left.

That is, in the sample production apparatus described in JP-A-2004-301853 and JP-A-2004-309499, although the relocation of the extraction sample that is the work piece can be performed in a short time, it is necessary to exchange the first stage and a second stage while being replaced. Therefore, the exchange of the stages is necessary every time the extraction sample is produced. The time taken in the exchange in a cases where plural samples are continuously worked on is inefficient.

The object of the present invention is to provide a stage for working, a focused beam working apparatus and a focused beam working method, in each of which the working can be performed with improved efficiency with the work piece being easily relocated.

SUMMARY OF THE INVENTION

In order to solve the above problems, the present invention provides the following means.

That is, a stage for working that is used when working on a work piece by irradiating a focused beam while observing the work piece in an observation region of a previously determined range, characterized by possessing a table having plural mount bases on whose upper faces there can be respectively mounted the work piece, and a rotation slant means rotating respectively the mount base about a Z-axis perpendicular to the upper face and slanting the upper face to an arbitrary angle, and in that the table is made possible to move so as to dispose respectively the plural mount bases to an inside of the observation region.

In the stage for working, which is concerned with this invention, since the table is made movable, the work piece mounted on the upper face of each mount base can be rapidly positioned respectively in the observation region. By this, the work piece mounted on each mount base can be worked with good efficiency while being observed, so that it is possible to raise an operation efficiency.

Further, it is also possible to easily relocate the work piece to other mount bases. For example, after the work piece mounted on one mount base is worked in the observation region, it is separated from the mount base by being retained by a manipulator or the like. Under this state by disposing other mount base in the observation region by moving the table, it is possible to easily relocate the work piece onto the other mount base.

Like this, since it is possible to dispose respectively each mount base in the observation region only by the movement of the table, it is also possible to easily perform a continuous working of the work piece, which requires hitherto a time, or the like, so that it is possible to contrive a shortening of working time and a reduction in manufacturing cost taken in the working.

Further, since there is possessed the rotation slant means, each mount base can be rotated about the Z-axis and slanted to the arbitrary angle. Therefore, when working the work piece in the observation region, the working can be performed by irradiating the focused beam from every direction, and thus a certainty in working operation increases and an easiness in use is raised, so that a convenience is good.

Further, a stage for working of the present invention is one characterized in that, in the stage for working of the present invention, the table is formed in a rectangular shape extending in one direction when seen from above, and the plural mount bases are arranged so as to be juxtaposed in one row along the one direction.

In the stage for working, which is concerned with this invention, since the plural mount bases are arranged in one row on the table, each mount base can be disposed in the observation region only by moving the table in one direction. Therefore, it is possible to contrive a simplification of a constitution and there becomes easy to operate.

Further, a stage for working of the present invention is one characterized by, in the stage for working of the present invention, possessing a retention means retaining the work piece in the observation region and separating it at least from the upper face of the mount base.

In the stage for working, which is concerned with this invention, since there is possessed the retention means, it is possible to easily relocate the work piece from one mount base to other mount base. That is, the work piece whose working in the observation region is finished is retained and separated from the upper face. Under this state, other mount base is positioned in the observation region by moving the table. And, by mounting the retained work piece to the upper face of other mount base, it is possible to easily perform the relocation.

By this, it is also possible to perform the working by combining the work piece mounted on one mount base with the work piece mounted on other mount base. Therefore, a width of the working operation widens, and the convenience is more raised.

Further, a stage for working of the present invention is one characterized by, in the stage for working of the present invention, possessing a slant means slanting the table to an arbitrary angle, and in that the retention means is made possible to slant together with the table.

In the stage for working, which is concerned with this invention, the table and the retention means slant together by the slant means under a state in which a mutual relative relation is maintained. Therefore, when the work piece is relocated by the retention means and contacted with the work piece mounted on other mount base to thereby temporarily junction the contact places by utilizing the focused beam, it is possible to irradiate the focused beam from every direction. Therefore, it is possible to accurately perform a temporal junction, and a working accuracy can be more raised.

Further, a focused beam working apparatus of the present invention is one characterized by possessing a stage for working according to any of the above inventions, an observation means observing the work piece disposed in the observation region, and an irradiation means irradiating the focused beam to the work piece disposed in the observation region.

In the focused beam working apparatus concerned with this invention, it is possible to perform the working of the work piece by irradiating the focused beam to the work piece by the irradiation means while observing the work piece disposed in the observation region by the observation means. In particular, by the stage for working, which has the movable table, since each mount base can be easily disposed respectively in the observation region, it is possible to easily perform the continuous working of the work piece, or the like. Accordingly, it is possible to contrive the shortening of working time and the reduction in cost taken in the working. Further, when performing the working, since the mount base can be rotated and slanted about the Z-axis by the rotation slant means, the work piece can be worked by irradiating the focused beam from every angle. Therefore, it is possible to perform the working of a high accuracy, and the certainty of the working operation is raised. Further, it is easy to use, and excellent in the convenience.

Further, a focused beam working method of the present invention is a focused beam working method working a work piece by irradiating a focused beam to the work piece under a state in which any one of plural mount bases on whose upper faces there is mounted the work piece is disposed in an observation region of a previously determined range, characterized by possessing a disposition process disposing any one of the mount bases in the observation region by moving a table having the plural mount bases, a rough working process roughly working, after the disposition process, the work piece by irradiating the focused beam while observing the work piece, a separation process separating, after the rough working process, the roughly worked work piece from the upper face of the mount base by being retained by a retention means, a movement process disposing, after the separation process, other mount base in the observation region by moving the table, a contact process approaching, after the movement process, the separated work piece toward the other mount base to thereby contact it with other work piece, and a fine working process irradiating, after the contact process, the focused beam to contact portions of the work piece and the other work piece to thereby bind both and finely work the roughly worked work piece, and in that, on occasions of the rough working process and the fine working process, the mount base is rotated about a Z-axis perpendicular to the upper face and slanted to an arbitrary angle.

In the focused beam working method concerned with this invention, by easily relocating the work piece, e.g., a diamond abrasive grain, mounted on the mount base to the other work piece, e.g., a cantilever side, mounted on the other mount base, it can be attached to a tip of the cantilever by utilizing a deposition film for instance.

That is, first, by the disposition process, the mount base on which the diamond abrasive grain is mounted is disposed in the observation region by moving the table. Subsequently, by the rough working process, there is selected one suitable (in a size, an external shape or the like) for a needle point by performing an observation of the diamond abrasive grain and, by irradiating the focused beam to the selected diamond abrasive grain, it is roughly worked to a shape suitable for the needle point. On this occasion, since the mount base can be rotated and slanted to the arbitrary angle, the focused beam can be irradiated from every direction, and it is possible to certainly perform the rough working.

Subsequently, by the separation process, the roughly worked diamond abrasive grain is retained by a retention means such as manipulator, and separated from the upper face of the mount base by being lifted. After the separation, by the movement process, the table is moved, and thereby the other mount base on which the cantilever is mounted is disposed in the observation region. After the movement of the table, there is performed the contact process in which the diamond abrasive grain is approached while being observed, and it is contacted with a predetermined position of a cantilever tip.

Subsequently, by the fine working process, the cantilever and the diamond abrasive grain are bound by the deposition film for instance by irradiating the focused beam, and the diamond abrasive grain is finely worked so as to become the needle point. On this occasion, similarly to the above-mentioned rough working process, since the rotation and the slant of the mount base are possible, the focused beam can be irradiated from every angle, and a junction can be made certain one by certainly forming the deposition film around the diamond abrasive grain.

Like this, the work piece can be worked while being easily relocated only by the movement of the table, so that it is possible to perform a working operation whose efficiency is good. In particular, only by the movement of the table, since each mount base can be disposed in the observation region, it is also possible to easily perform the continuous working of the work piece, which requires hitherto the time, so that it is possible to contrive the shortening of working time and the reduction in cost taken in the working.

Further, a focused beam working method of the present invention is a focused beam working method working a work piece by irradiating a focused beam to the work piece under a state in which any one of plural mount bases, on whose upper faces the work piece is mounted, is disposed in an observation region of a previously determined range, characterized by possessing a disposition process disposing any one of the mount bases in the observation region by moving a table having the plural mount bases; a production process producing, after the disposition process, a work piece small piece from the work piece by irradiating the focused beam while observing the work piece; a separation process separating, after the production process, the work piece small piece from the upper face of the mount base by being retained by a retention means; a movement process disposing, after the separation process, other mount base in the observation region by moving the table; a contact process approaching, after the movement process, the separated work piece small piece toward the other mount base to thereby contact it with other work piece mounted on the upper face; and a binding process irradiating, after the contact process, the focused beam to contact portions of the work piece small piece and the other work piece to thereby bind both. During the production process and the binding process, the mount base is rotated about a Z-axis perpendicular to the upper face and slanted to an arbitrary angle.

In the focused beam working method concerned with this invention, it is possible to manufacture a TEM observation sample by producing a sample piece that is the work piece small piece from the work piece, e.g., a sample, mounted on the mount base, easily relocating the sample piece to the other work piece, e.g., a sample holder, mounted on the other mount base, and attaching it by utilizing the deposition film.

That is, first, by the disposition process, the mount base on which the sample is mounted is disposed in the observation region by moving the table. Subsequently, by the production process, the sample is cutting-worked by irradiating the focused beam to a predetermined position while being observed, thereby producing the sample piece. On this occasion, since the mount base can be rotated and slanted to the arbitrary angle, the focused beam can be irradiated from every direction, and it is possible to certainly produce the sample piece of an arbitrary shape.

Subsequently, by the separation process, the produced sample piece is retained by the retention means such as manipulator, and separated from the upper face of the mount base by being lifted. After the separation, by the movement process, the table is moved, and thereby the other mount base on which the sample holder is mounted is disposed in the observation region. After the movement of the table, there is performed the contact process in which the sample piece is approached to the sample holder while being observed, and it is contacted with a predetermined position of sample holder.

Subsequently, by the binding process, by the fact that the sample piece and the sample holder are bound by the deposition film for instance by irradiating the focused beam, it is possible to manufacture the TEM observation sample. On this occasion, similarly to the above-mentioned production process, since the rotation and the slant of the mount base are possible, the focused beam can be irradiated from every angle, and the junction can be made certain one by certainly forming the deposition film around the sample piece.

Like this, the work piece can be worked while being relocated easily only by the movement of the table, so that it is possible to perform the working operation whose efficiency is good. In particular, only by the movement of the table, since each mount base can be disposed in the observation region, it is also possible to easily perform the continuous working of the work piece, which requires hitherto the time, so that it is possible to contrive the shortening of working time and the reduction in cost taken in the working.

ADVANTAGES OF THE INVENTION

According to the stage for working, which is concerned with the present invention, since each mount base can be positioned respectively in the observation region only by the movement of the table, it is also possible to easily perform the continuous working of the work piece, which requires hitherto the time, or the like, so that it is possible to contrive the shortening of working time and the reduction in manufacturing cost taken in the working.

Further, according to the focused beam working apparatus concerned with the present invention, it is possible to perform the working of the work piece by irradiating the focused beam to the work piece from the irradiation means while observing the work piece positioned in the observation region by the observation means. In particular, by the stage for working, which has the movable table, since each mount base can be easily positioned respectively in the observation region, it is possible to easily perform the continuous working of the work piece, or the like, so that it is possible to contrive the shortening of working time and the reduction in cost taken in the working.

Further, according to the focused beam working method of the present invention, the work piece can be worked while being relocated easily only by the movement of the table, so that it is possible to perform the working operation whose efficiency is good. In particular, only by the movement of the table, since each mount base can be disposed in the observation region, it is also possible to easily perform the continuous working of the work piece, which requires hitherto the time, so that it is possible to contrive the shortening of working time and the reduction in cost taken in the working.

DETAILED DESCRIPTION OF THE PREFERRED EMBODIMENTS

Explained below with reference to FIGS. 1-4 is an embodiment of a stage for working, a focused beam working apparatus and a focused beam working method.

In the present embodiment a work piece is made by a diamond abrasive grain and a cantilever, where the diamond abrasive grain is attached to, for example, a tip of the cantilever.

Figure 1:
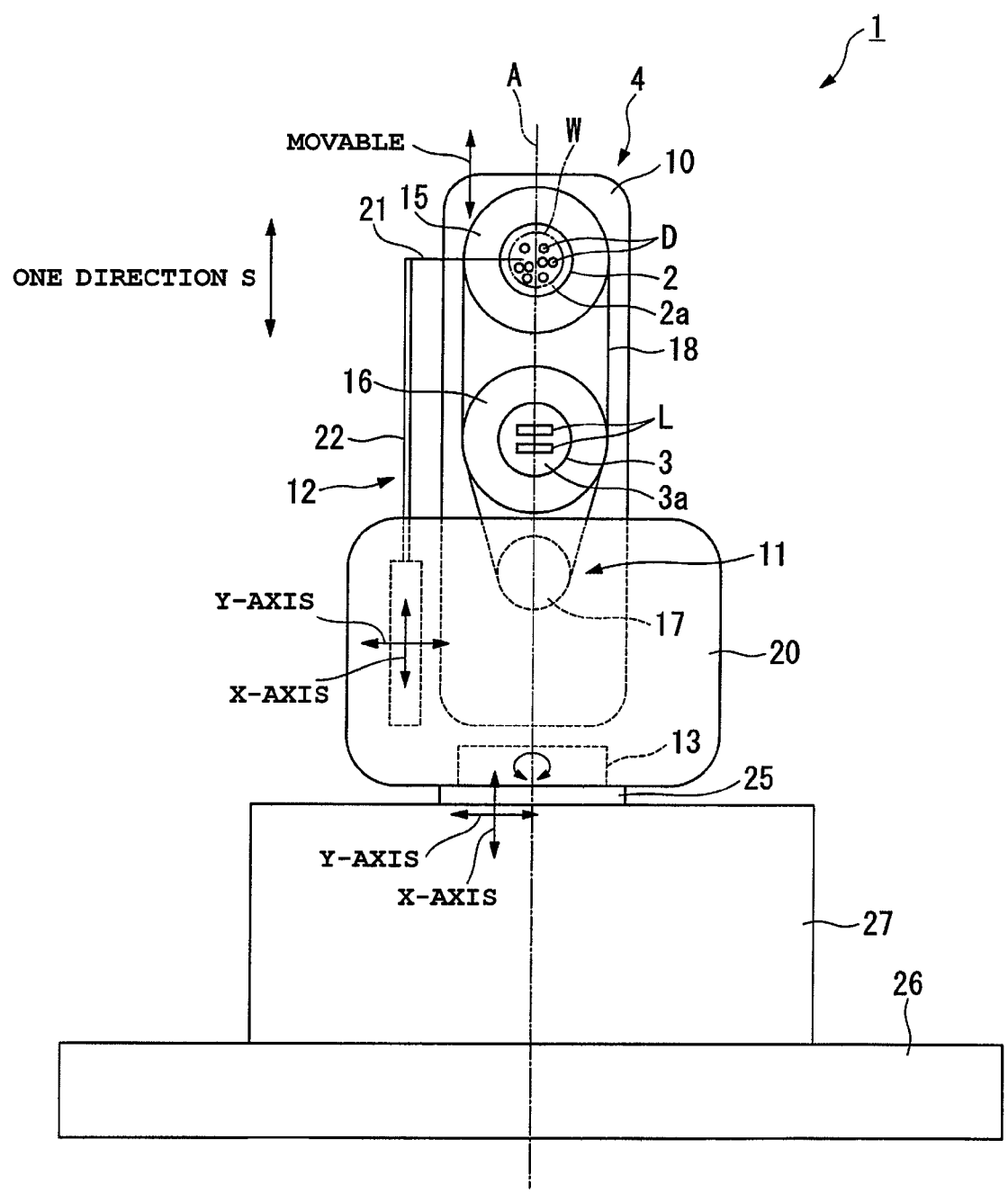
FIG. 1 is a top view showing one embodiment of a focused beam working apparatus having a stage for working, which is concerned with the present invention, wherein there is shown a state in which an upper face of a first sample port is positioned in an observation region.
Figure 2:
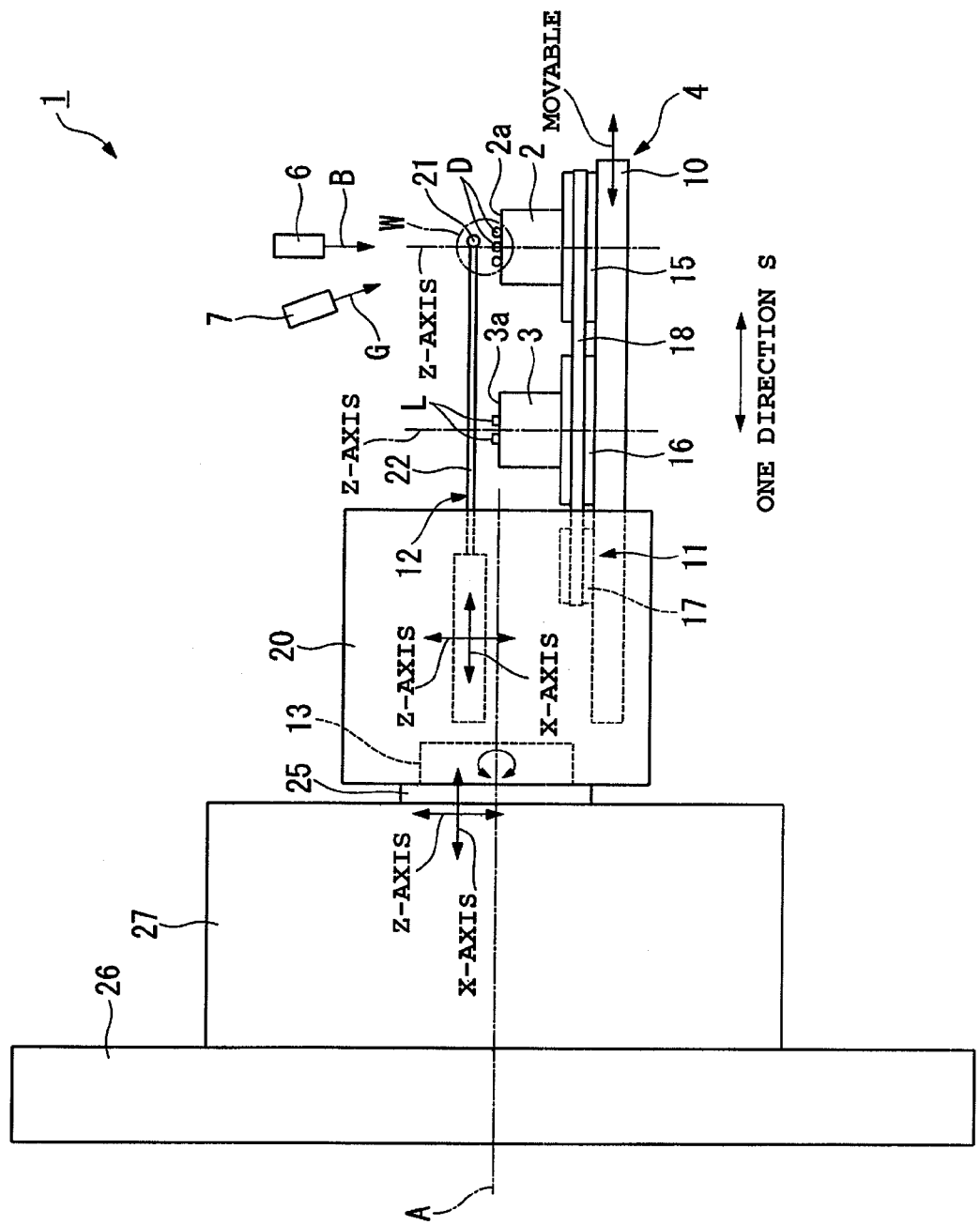
FIG. 2 is a side view of the state shown in FIG. 1.

As shown in FIG. 1 and FIG. 2, a focused beam working apparatus 1 of the present embodiment possesses a stage 4 for working, which has a first sample port (mount base) 2 on whose upper face 2a there is mounted a diamond abrasive grain D, and a second sample port (mount base) 3 on whose upper face 3a there is mounted a cantilever L. The apparatus 1 further includes an observation means not shown in the drawing, in which the diamond abrasive grain D or the cantilever L, and which is disposed in an observation region W, is observed, an irradiation part (irradiation means) 6 irradiating a focused beam B such as FIB to the diamond abrasive grain D or the cantilever L, which is disposed in the observation region W, and a gas supply source 7 supplying a raw material gas G forming a deposition film in the observation region W.

The stage 4 for working is one used when working by irradiating the focused beam B while observing the diamond abrasive grain D or the cantilever L in the observation range W of a previously determined range. The stage 4 possesses a table 10 having the first sample port 2 and the second sample port 3, a rotation slant means 11 rotating respectively the first sample port 2 and the second sample port 3 about a Z-axis perpendicular to the upper faces 2a and 3a, and slanting the upper faces 2a and 3a to an arbitrary direction, a retention means 12 retaining the diamond abrasive grain D or the cantilever L in the observation range W, and separating it at least from the upper face 2a of the first sample port 2 or the upper face 3a of the second sample port 3, and a tilt mechanism (slant means) 13 slanting the table 10 to an arbitrary angle.

The first sample port 2 and the second sample port 3 are formed like a circular cylinder (circle in section) of 10 mm in diameter and 10 mm in height for instance. Further, the first sample port 2 and the second sample port 3 are respectively attached to a first rotation base 15 and a second rotation base 16, which are formed like a disc, so as to be capable of slanting under a state in which their centers are aligned. That is, there is made such that the first sample port 2 and the second sample port 3 are slanted (tilted) at an arbitrary angle, e.g., in a range of 0°-90°, with their lower face sides being spherical-surface-supported by tilt mechanisms not shown in the drawing, which are provided inside the first rotation base 15 and the second rotation base 16.

The table 10 is formed in an approximately rectangular shape extending in one direction S when seen from above. And, the first rotation base 15 and the second rotation base 16 are rotatably attached onto the table 10 under a state in which they are spaced by a predetermined interval in the one direction S. That is, the first sample port 2 and the second sample port 3 are disposed so as to be juxtaposed in one row along the one direction S of the table 10.

Further to the table 10, there is attached a motor shaft 17 rotation-driven by a motor not shown in the drawing. This motor shaft 17 is attached while adjoining the second rotation base 16 in such a manner that its rotation center coincides with an axis line. A connecting rotation centers of the first rotation base 15 and the second rotation base 16. And, a rotation belt 18 is wound so as to butt respectively against outer periphery faces of the motor shaft 17, the first rotation base 15 and the second rotation base 16. Accordingly, if the motor shaft 17 is rotated, the first rotation base 15 and the second rotation base 16 are rotated together about the Z-axis toward the same direction. Further, following rotation operations of the first rotation base 15 and the second rotation base 16, the first sample port 2 and the second sample port 3 are also rotated similarly.

That is, the tilt mechanism, the motor shaft 17, the rotation belt 18, the first rotation base 15 and the second rotation base 16 constitute the above rotation slant means 11.

Further, the table 10 is movably attached to an attachment pedestal 20 formed like a box. The direction of this movement is along a direction of the axis line A. Accordingly, the table 10 can dispose respectively the first sample port 2 and the second sample port 3 in the above observation region W.

Further, to the attachment pedestal 20, there is attached a prober 22 having in its tip a needle prober 21 for transplantation. This prober 22 is made three-dimensionally movable toward a direction of the Z-axis and an XY-direction perpendicular to the Z-axis, and made in such a manner that it can adjust such that the tip of the needle prober 21 for transplantation enters into the observation region W. Further, the diamond abrasive grain D and the cantilever L can be fixed to and retained by the tip of the needle prober 21 for transplantation using the deposition film. That is, the needle prober 21 for transplantation and the prober 22 constitute the above retention means 12.

Further, the attachment pedestal 20 is attached to a tip of an arm 25 capable of expanding and contracting toward the XY-axis direction so as to be capable of rotating about the axis line A. Concretely, it is attached to the tip of the arm 25 through the above tilt mechanism 13, and made so as to be capable of slanting (tilting) in a range of ±60 degrees.

There is made such that, by this tilt mechanism 13, the table 10 and the retention means 12 are slanted together under a state in which they maintain a mutual, relative relation.

Further, a base end side of the arm 25 is attached to a base 27 fixed to a front face flange 26 so as to be movable toward the Z-axis direction. In other words, the attachment pedestal 20 is made movable toward three directions of XYZ-axes via the arm 25.

An explanation will be presented about a focused beam working method in which, by the focused beam working apparatus 1 constituted like this, the diamond abrasive grain D mounted on the first sample port 2 is relocated to the second sample port 3 side and fixed to a tip of the cantilever L.

The focused beam working method of the present embodiment is one which possesses a disposition process disposing the first sample port 2 on which the diamond abrasive grain D is mounted in the observation region W by moving the table 10; a rough working process roughly working, after the disposition process, the diamond abrasive grain D by irradiating the focused beam B while observing the diamond abrasive grain D; a separation process separating, after the rough working process, the roughly worked diamond abrasive grain D from the upper face 2a of the first sample port 2 by being retained by the retention means 12; a movement process disposing, after the separation process, the second sample port 3 in the observation region W by moving the table 10; a contact process approaching, after the movement process, the separated diamond abrasive grain D toward the second sample port 3 (other mount base) to thereby contact it with the cantilever L (other work piece) mounted on the upper face 3a; and a fine working process irradiating, after the contact process, the focused beam B to contact portions of the diamond abrasive grain D and the cantilever L to thereby bind both and finely work the roughly worked diamond abrasive grain D, and in which, on occasions of the rough working process and the fine working process, the first sample port 2 and the second sample port 3 are rotated about the Z-axis and slanted to the arbitrary angle.

Each of these processes is explained in more detail below.

First, plural diamond abrasive grains D are mounted to the upper face 2a of the first sample port 2, and plural cantilevers L are mounted to the upper face 3a of the second sample port 3. Subsequently, after the attachment pedestal 20 is roughly moved in the three directions through the arm 25, the above disposition process is performed disposing the first sample port 2 on which the diamond abrasive grain D is mounted in the observation region W by moving the table 10. Accordingly, it is possible to perform, by the observation means, an observation of the plural diamond abrasive grains D mounted to the upper face 2a of the first sample port 2. By this observation, there is selected one (e.g., one whose size, external shape or the like is optimum) suitable for a needle point from among the plural diamond abrasive grains.

By irradiating the focused beam B to the selected diamond abrasive grain D from the irradiation part 6, the diamond abrasive grain D is roughly worked such that its shape becomes a desired shape. On the occasion of this rough working, by the rotation slant means 11, since the first sample port 2 can be rotated about the Z-axis and the upper face 2a can be tilted so as to become the arbitrary angle, it is possible to certainly, roughly work the diamond abrasive grain D to a desired shape. In addition, based on the fact that a working circumstance of the diamond abrasive grain D can be observed by the observation means, the rough working of the diamond abrasive grain D can be certainly performed.

After the rough working, by three-dimensionally moving the needle prober 21 for transplantation by the prober 22, the tip of the needle prober 21 for transplantation is contacted with the diamond abrasive grain D after the rough working. And, by supplying the raw material gas G from the gas supply source 7 and irradiating the focused bean B, the deposition film is formed, and the tip of the needle prober 21 for transplantation and the diamond abrasive grain D are fixed (retained). After the fixation, by moving the prober 22, there is performed the above separation process separating the diamond abrasive grain D from the upper face 2a of the first sample port 2.

Figure 3:
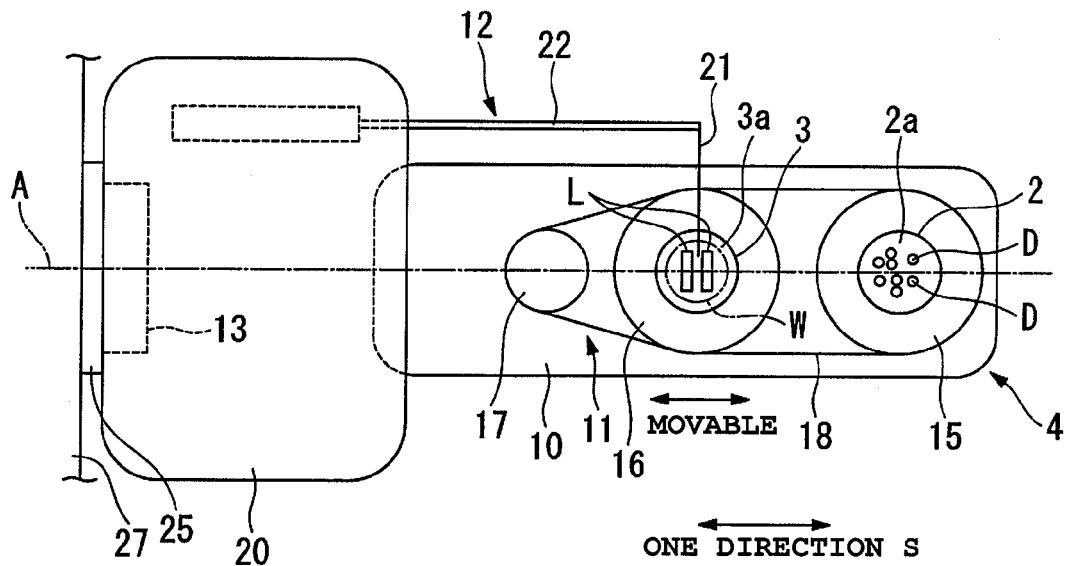
FIG. 3 is a top view showing a state in which a table of the focused beam working apparatus shown in FIG. 1 is moved and an upper face of a second sample port is positioned in the observation region.
Figure 4:
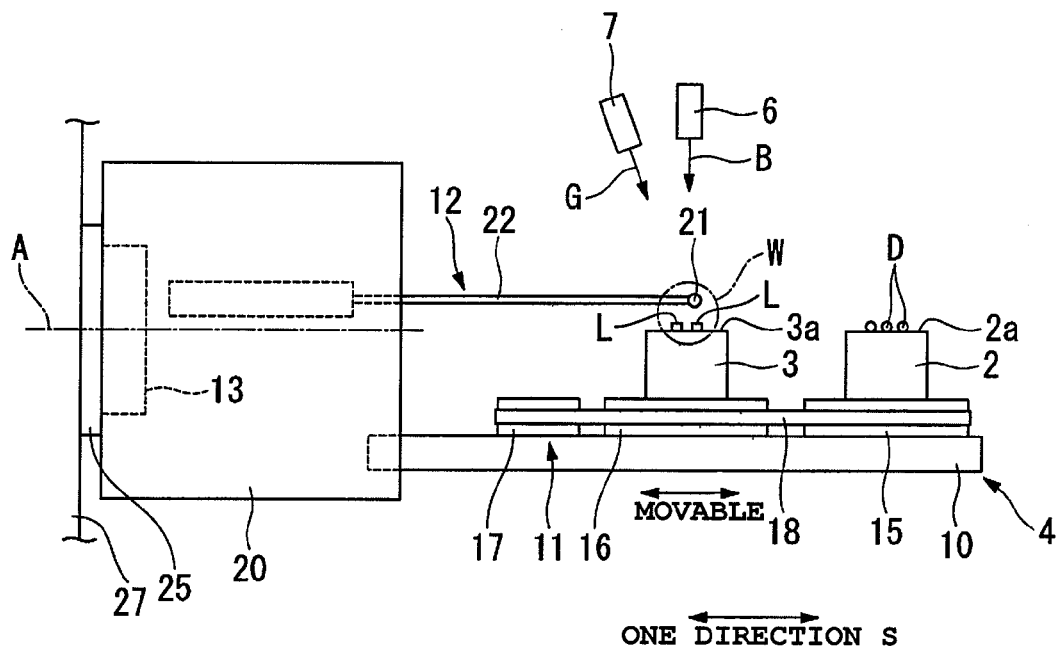
FIG. 4 is a side view of the state shown in FIG. 3.

As shown in FIG. 3 and FIG. 4, after the separation, by moving the table 10 in the one direction S, i.e., the axis line A direction, the above movement process is performed disposing the second sample port 3 to which the cantilever L is mounted in the observation region W. By operating the prober 22 while observing by the observation means, there is performed the above contact process contacting the diamond abrasive grain D fixed to the tip of the prober 22 for transplantation with the tip of the cantilever L.

Under this state, by forming the deposition film again, the cantilever L and the diamond abrasive grain D are temporarily fixed. In particular, on this occasion, since the table 10 and the retention means 12 can be slanted about the axis line A by the tilt mechanism 13 under a state in which their mutual, positional relation is maintained, it is easy to set the deposition film to a desired position without undergoing an influence of the needle prober 21 for transplantation. Therefore, there is no positional deviation or the like, and it is possible to certainly perform a temporary fixation, so that it leads to a raise in working accuracy.

After the above temporary fixation is finished, by etching the deposition film fixing the needle prober 21 for transplantation and the diamond abrasive grain D by irradiating the focused beam B, a retention by the retention means 12 is released. After releasing the retention, again by the supply of the raw material gas G and the irradiation of the focused beam B, the diamond abrasive grain D is completely attached to the tip of the cantilever L to thereby bind both, and there is performed the above fine working process finely working such that the roughly worked diamond abrasive grain D becomes completely the needle point.

In particular, on the occasion of this fine working process, similarly to a time of the above rough working process, since the rotation and the slant of the second sample port 3 are possible by the rotation slant means, a junction can be made complete one by completely forming the deposition film around the diamond abrasive grain D and the fine working can be certainly performed.

By performing each of these processes, it is possible to manufacture the cantilever L having in its tip the diamond abrasive grain D becoming the needle point.

As mentioned above, according to the focused beam working apparatus 1 and the focused beam working method of the present embodiment, it is possible to perform the working by irradiating the focused beam B from the irradiation part 6 while observing, by the observation means, the diamond abrasive grain D or the cantilever, which is disposed in the observation region W. In particular, since there is possessed the stage 4 for working, which has the movable table 10, it is possible to easily perform the relocation of the diamond abrasive grain D only by the movement of the table 10 with the first sample port 2 and the second sample port 3 being respectively disposed in the observation region W without putting out the diamond abrasive grain D and the cantilever L to an outside of the apparatus even only one time, so that it is possible to perform a working operation whose efficiency is good. In addition, the continuous working hitherto requiring the time can be easily performed, so that it is possible to contrive the shortening of working time and the reduction in manufacturing cost taken in the working.

Further, since the first sample port 2 and the second sample port 3 are arranged on the table 10 while being juxtaposed in one row, the first sample port 2 and the second sample port 3 can be disposed in the observation region W only by moving the table 10 in the one direction S. Therefore, it is possible to contrive a simplification in constitution, and there becomes easy to operate.

Incidentally, a technical scope of the present invention is not one limited to the above embodiment, and it is possible to add various modifications in a scope not deviating from a gist of the present invention.

For example, although there is made the constitution in which the two mount bases, i.e., the first sample port 2 and the second sample port 3, are provided on the table 10, the present invention is not limited to this, and there may be provided three or more mount bases for instance.

Further, although there is shown the example in which the diamond abrasive grain D and the cantilever L are adopted as the work piece, and the diamond abrasive grain D is attached to the cantilever L, it is not one limited to this case. For example, an observation sample for TEM may be produced by adopting a sample and a sample holder as the work piece, producing a sample piece from the sample by the focused beam B, and fixing the sample piece to the sample holder by being relocated.

A focused beam working method in this case possesses a disposition process disposing the first sample port 2 on whose upper face 2a the sample is mounted in the observation region W by moving the table 10; a production process producing, after the disposition process, the sample piece (work piece small piece) from the sample by irradiating the focused beam B while observing the sample; a separation process separating, after the production process, the sample piece from the upper face 2a of the first sample port 2 by being retained by the retention means 12; a movement process disposing, after the separation process, the second sample port 3 in the observation region W by moving the table 10; a contact process approaching, after the movement process, the separated sample piece toward the second sample port 3 to thereby contact it with the sample holder mounted on the upper face 3a; and a binding process irradiating, after the contact process, the focused beam B to contact portions of the sample piece and the sample holder to thereby bind both, and there suffices if, on occasions of the production process and the binding process, the first sample port 2 and the second sample port 3 are rotated about the Z-axis and slanted to the arbitrary angle.

If explained in more detail, first, by moving the table 10 by the disposition process, the first sample port 2 on which the sample is mounted is disposed in the observation region W. Subsequently, by the production process, a cutting working is performed by irradiating the focused bean B to a predetermined position while observing the sample, thereby producing the sample piece. On this occasion, since the first sample port 2 can be rotated and slanted to the arbitrary angle, the focused beam B can be irradiated from every angle, so that it is possible to certainly produce the sample piece of an arbitrary shape.

Subsequently, by the separation process, the produced sample piece is retained by the retention means 12, and separated from the upper face 2a of the first sample port 2 by being lifted. After the separation, by moving the table 10 by the movement process, the second sample port 3, in which the sample holder is mounted in the observation region W, is disposed. After the movement of the table 10, the sample piece is approached to the sample holder while observing, thereby performing the contact process contacting it with a predetermined position of the sample holder.

Subsequently, by the binding process, by binding the sample piece and the sample holder by the deposition film for instance by irradiating the focused beam B, it is possible to manufacture the observation sample for TEM.

On this occasion, similarly to the above-mentioned production process, since the rotation and the slant of the second sample port 3 are possible, the focused beam B can be irradiated from every angle, and the junction can be made certain one by certainly forming the deposition film around the sample piece.

Also in this case, similarly to the working time of the diamond abrasive grain D, since the sample piece can be easily worked while being relocated only by the movement of the table 10, it is possible to perform the working operation whose efficiency is good. Further, the continuous working hitherto requiring the time can be easily performed, so that it is possible to contrive the shortening of working time and the reduction in cost taken in the working.

In the stage for working of the focused beam apparatus, since each mount base can be respectively positioned in the observation region only by the movement of the table, also the continuous working hitherto requiring the time, or the like can be easily performed, so that it is possible to contrive the shortening of working time and the reduction in manufacturing cost taken in the working.

What is claimed is:

1. A stage for working a work piece by irradiating a focused beam while observing the work piece in an observation region of a previously determined range, comprising:
   a table having plural mount bases arranged so as to be juxtaposed in one row along a first direction, and
   a retention means retaining the work piece in the observation region and separating the work piece at least from an upper face of at least one of the mount bases; and
   a tilt means for rotating the table around a first axis extending in the first direction to an arbitrary angle such that the retention means slants together with the table while maintaining a mutual relative positional relationship between the table and the retention means.

2. A stage for working according to claim 1, characterized in that:
   the table comprises a rectangular shape extending in one direction when seen from above.

3. A focused beam working apparatus comprising:
   a stage for working according to claim 1,
   an observation means observing the work piece disposed in the observation region, and
   an irradiation means irradiating the focused beam to the work piece disposed in the observation region.

4. A focused beam working method, comprising:
   disposing one of plural mount bases in an observation region by moving a table having the plural mount bases,
   separating a worked work piece from an upper face of the mount bases,
   disposing a second mount base of the plural mount bases in the observation region by moving the table with the work piece retained by a retention means,
   moving the separated work piece toward the second mount base to thereby bring the separated work piece in contact with a second work piece mounted on an upper face of the second mount base, and
   irradiating a focused beam to bind the work piece and the second work piece, and
   wherein during the irradiating the mount bases are tilted to a first angle under a state in which a mutual relative positional relationship between the table and the retention means is maintained.

5. A focused beam working method, comprising:
   disposing one of plural mount bases in an observation region by moving a table having the plural mount bases,
   producing a sample piece from the work piece by irradiating the focused beam while observing the work piece, separating the sample piece from an upper face of the one of the plural mount bases;

disposing a second mount base of the plural mount bases in the observation region by moving the table with the sample piece retained by a retention means, moving the separated sample piece toward the second mount base to thereby bring the separated sample piece in contact with a second work piece mounted on an upper face of the second mount base, and irradiating the focused beam to bind the sample piece and the second work piece; and wherein during the irradiating, the mount bases are tilted to a first angle under a state in which a mutual relative positional relationship between the table and the retention means is maintained.

* * * * *